United States Patent [19]
Fukuda et al.

[11] Patent Number: 5,719,666
[45] Date of Patent: Feb. 17, 1998

[54] PARTICLE ANALYZER CLASSIFYING PARTICLES OF VARIOUS BIOLOGICAL TYPES USING A CORRELATION OF MEASUREMENTS

[75] Inventors: Masakazu Fukuda; Hiroyuki Nakamoto; Masaaki Oka, all of Hyogo, Japan

[73] Assignee: Toa Medical Electronics Co., Ltd., Hyogo, Japan

[21] Appl. No.: 557,576

[22] Filed: Nov. 14, 1995

[30] Foreign Application Priority Data

Nov. 14, 1994 [JP] Japan .................. 6-279490

[51] Int. Cl.$^6$ .................. G01N 21/00; G01J 3/30
[52] U.S. Cl. .................. 356/72; 356/73; 356/317; 356/338; 356/341
[58] Field of Search .................. 356/72, 73, 317–318, 356/335–343, 442; 324/73.1

[56] References Cited

U.S. PATENT DOCUMENTS

| | | |
|---|---|---|
| 3,826,364 | 7/1974 | Bonner et al. . |
| 4,198,160 | 4/1980 | Kachel et al. .................. 356/72 |
| 4,298,836 | 11/1981 | Groves et al. . |
| 4,661,913 | 4/1987 | Wu et al. .................. 356/442 |
| 5,059,395 | 10/1991 | Brittenham et al. . |
| 5,351,118 | 9/1994 | Spinell .................. 356/72 |

FOREIGN PATENT DOCUMENTS

| | | |
|---|---|---|
| 0121261 | 3/1984 | European Pat. Off. . |
| 0242971 | 10/1987 | European Pat. Off. . |
| 5150991 | 5/1992 | European Pat. Off. . |
| 5489831 | 12/1992 | European Pat. Off. . |
| 1-250037 | 10/1989 | Japan . |
| 4-337459 | 11/1992 | Japan . |
| WO9012308 | 10/1990 | WIPO . |

OTHER PUBLICATIONS

John A. Steinkamp, Flow Cytometry, 8127 Review of Scientific Instruments; 55, (1984) Sep., No. 9, New York, USA.

*Primary Examiner*—Frank G. Font
*Assistant Examiner*—Jason D. Vierra Eisenberg

[57] ABSTRACT

A particle analyzer includes a flow cell including first and second cells for containing an electrolyte with various types of biological particles floating therein. The first and second cells are connected to each other by a pore to allow the particles to flow from the first cell to the second cell through the pore. A first and a second electrode are provided in the electrolyte in the first and second cells respectively. A first detector detects an electric resistance between the first and second electrodes which changes according as the particle passes through the pore to generate an electric resistance signal representative of the electric resistance. A light source emits a beam of light to the flowing particle and a second detector detects scattered light from the particle receiving the beam of light to generate a scattered light signal representative of an intensity of the scattered light. A clock device clocks a period of time during which the scattered light signal is generated. An analyzer classifies the particle as a particular type of biological particle based on a correlation between the electric resistance signal and the clocked period of time.

18 Claims, 9 Drawing Sheets

FIG. 1

Epithelium cell   Mucous string   Cast

FIG. 2

Electric resistance maximum value (volume data)

- Cast
- Mucous string
- Epithelium cell

Scattered light pulse width (length data)

FIG. 4

- Cast
- Mucous string
- Epithelium cell
- Leukocyte

Scattered light pulse width I

FIG. 5

- Cast
- Mucous string

Scattered light pulse width (length data)

FIG.6(a) Epithelium cell

FIG.6(b) Mucous string

FIG.6(c) Cast

FIG. 7

FIG. 8(a)  
Glassy cast

FIG. 8(b)  
Cast containing inclusion bodies

Glassy cast

FIG.10(b)

Cast containing inclusion bodies

PARTICLE ANALYZER CLASSIFYING PARTICLES OF VARIOUS BIOLOGICAL TYPES USING A CORRELATION OF MEASUREMENTS

BACKGROUND OF THE INVENTION

1. Field of the Invention

The present invention relates to particle analyzers, more particularly to particle analyzers for detecting particle components contained in urine such as casts, mucous strings and the like.

2. Description of Related Art

Conventional particle analyzers of the kind include an optical particle analyzer which measure forward or side fluorescence and forward or side scattered light obtained by emitting light to dyed particles; a particle counting device which counts various sizes of particles by inserting a needle-shaped member into the orifice of the electric resistance type particle counting device (see, for example, Japanese Unexamined Patent Publication No. HEI 4(1992)-337459 and European Patent Application No. 242971-A2); and a diagnosing device for diagnosing an anemia by measuring the pulse height and the pulse width of electric resistance signals of erythrocytes (see, for example, Japanese Unexamined Patent Publication No. HEI 1(1989)-250037 and U.S. Pat. No. 5059395).

Also devices combining the optical and electric resistance methods are known.

It is believed that the reason why the devices combining the optical and electric resistance methods have been conceived is that the conventional optical particle analyzers are incapable of determining the volume of a particle accurately. Then particle analyzers have been invented which are capable of obtaining both optical data such as scattered light data and electric resistance data correlative to the volume of a particle, by providing an orifice for detecting changes in electric resistance (see, for example, U.S. Pat. No. 4,298,836). Unfortunately, such a detector, though it is capable of measuring the volume of a spherical particle accurately, needs an additional treatment such as adjustment of the shape for obtaining the accurate volume of a spheroidal particle, and is incapable of measuring the accurate volume of a particle which is larger than the size of the electric resistance detecting region, namely the aperture part through which the particle passes.

Also when large solid components in urine such as epithelium cells, casts, mucous strings which are longer than 100 μm in length are classified by the conventional electric resistance detecting analyzer, the size of the particle detecting region has to be larger than any object to be measured in order to obtain the accurate volume of the solid component. Consequently, the pulse height of the detected signal correlates with the pulse width thereof and the pulse width of the electric resistance signal is not significant any more. In addition, it is impossible for such an analyzer to discriminate the solid components such as epithelium cells and casts which are nearly the same in volume and length.

SUMMARY OF THE INVENTION

The present invention has been conceived in view of the above mentioned problems, and an object of the present invention is to provide a particle analyzer to electrically detect data about the volume of particles and at the same time optically detect data about the length of the particles, then to classify the particles based on the correlation of the obtained data.

The present invention provides a particle analyzer comprising; a flow cell including first and second cells for containing electrolyte, the first and second cells being connected to each other by a pore to allow particles to flow from the first cell to the second cell through the pore; a first and a second electrode provided in the electrolyte in the first and second cells respectively; a first detector for detecting an electric resistance between the first and second electrodes which changes according as the particle passes through the pore to generate an electric resistance signal representative of the electric resistance; a light source for emitting a beam of light to the flowing particle; a second detector for detecting scattered light from the particle receiving the beam of light to generate a scattered light signal representative of an intensity of the scattered light; a clock mean for clocking a period of time during which the scattered light signal is generated; and an analyzer for classifying the particle based on a correlation between the electric resistance signal and the clocked period of time.

DESCRIPTION OF THE PREFERRED EMBODIMENTS

The particle analyzer of the present invention serves to determine particle components contained in urine, mainly in human urine, such as casts, mucous strings, epithelium cells and the like. The particles to be analyzed may be pretreated with a fluorescent dye or a fluorescent labeling reagent.

The cast has a base of mucoprotein which coagulates and precipitates in a renal tubule in the presence of plasma protein with sanguineous cells, renal tubule epithelium cells and the like included in the base. The cast is called a cylinder from its shape or is given the name because it is formed by a renal tubule as a cast. The existence of a cast means that a temporary obstruction has existed in a renal tubule, being an important finding suggesting a disease in renal parenchyma. Particularly a cast including sanguineous cells, epithelium casts or the like is clinically significant.

The mucous string is a long, thin string which resembles a glassy cast with the both ends extending as a long line. A few found in normal human urine, a lot of mucous strings are found in urine of a chronic ureteritis patient or a chronic urocystitis patient.

The flow cell of the present invention is provided with two cells for containing electrolyte which are connected to each other by a pore. Aptly, in the flow cell, a sample liquid including particle components flows wrapped in sheath liquid, forming a current by hydrodynamics effects in such a way that the particles pass one after another through the pore.

The flow cell of the present invention is to allow sample liquid to flow through the pore at the speed of about from 0.5 to 10 m/sec.

Preferably the sample and the sheath liquid have the same electric conductivity.

The first and the second electrodes are formed of an electrically-conductive material, preferably formed of platinum or stainless steel in view of their resistance to corrosion.

A first detector means serves to detect the change of the electric resistance between the first and the second electrodes when a particle passes through the pore. The first detector means is preferably provided with a current source for providing the first and the second electrodes with electric current and provided with a detecting device for detecting the electric current flowing between the first and the second electrodes.

The electric resistance signal obtained by the first detecting shows a mountain-shaped pulse waveform when a particle passes through the pore. As is known, the pulse height is almost in proportion to the volume of the particle.

The light source serves to emit a beam of light from the outside of the flow cell to a particle just before it passes through the pore, while it is passing through the pore, or just after it has passed through the pore. It is preferable to use for the light source a laser light source which emits light continuously, but not pulsingly, with a condenser lens added. The emitted beam width in the flow direction is preferably from 5 to 30 μm.

The second detecting means serves to detect the scattered light from a particle receiving the light beam and generate a scattered light signal representative of the scattered light. A photodiode, a phototransistor and a photomultiplier tube can be used for the second detector.

Figure 3A:
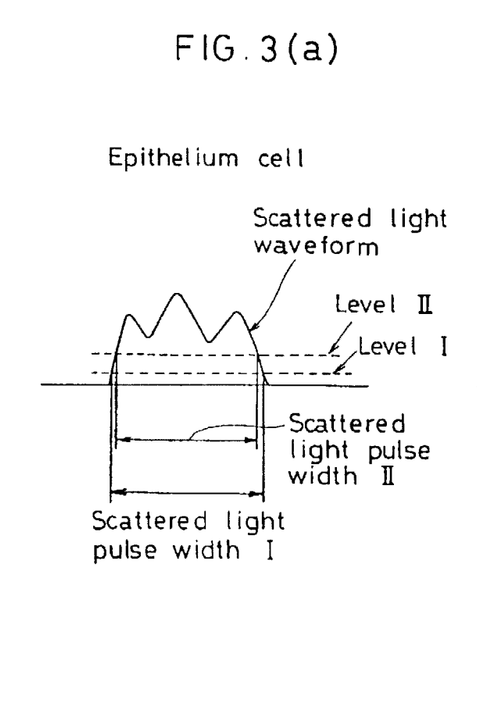
FIGS. 3(a) to 3(c) are views explaining waveforms of scattered light signals and the pulse widths thereof in accordance with the present invention.
Figure 3B:
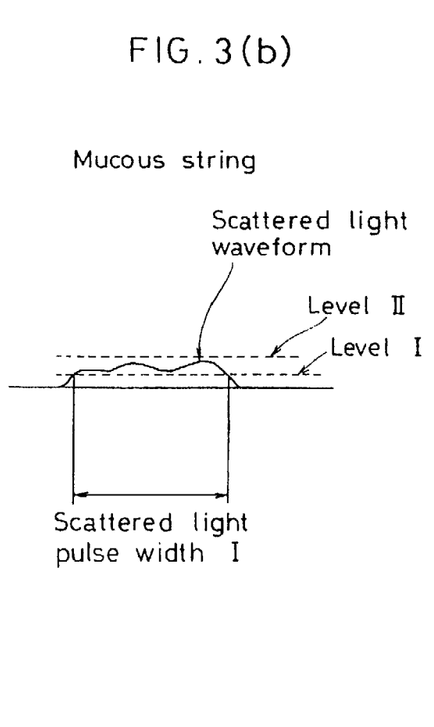
Figure 3C:
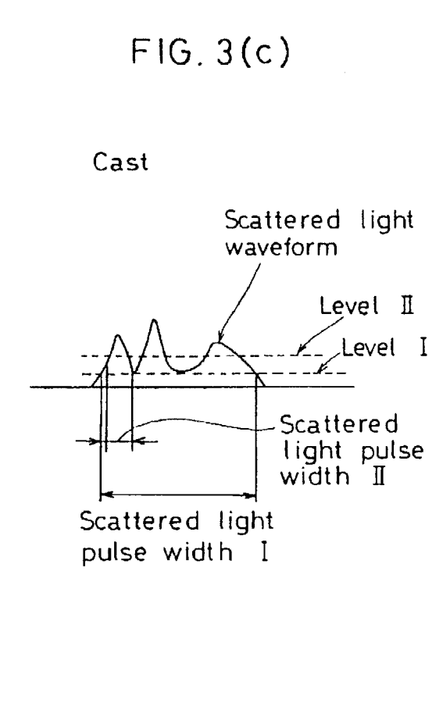

The clock serves to clock a period of time during which the scattered light signal is generated, namely a pulse width. That is, the clock clocks a period of time from the beginning to the end of detection of the scattered light performed by the second detector. A counter, or a timer, and a comparator which has a suitable threshold, e.g. level 1 in FIG. 3, can be used for the clock.

The period of time during which the scattered light signal is generated, i.e. the pulse width, reflects the length of the particle in the flow direction.

Figure 1:
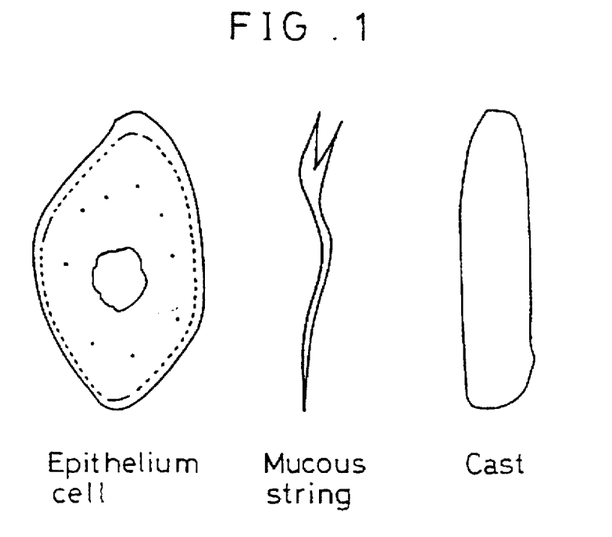
FIG. 1 illustrates side views of an epithelium cell, a mucous string, and a cast contained in urine.

Because an epithelium cell, a mucous string and a cast have shapes as shown in FIG. 1, the flowing inequality is true to the ratios of the volume to the length, i.e. the volume / the length, of each of these particle components:

the epithelium cell>the cast>the mucous string.

Figure 2:
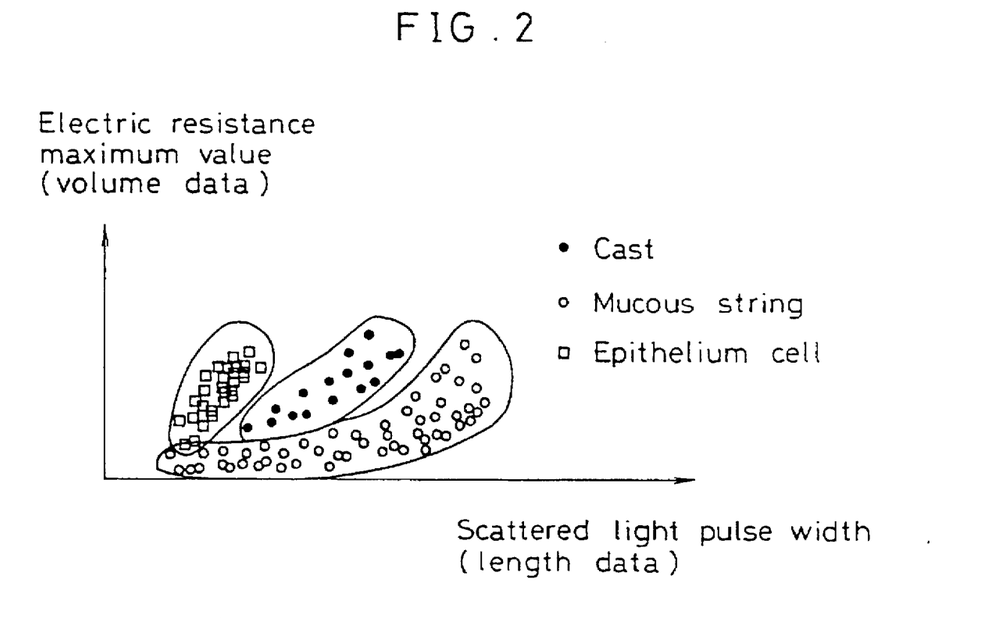
FIG. 2 is a graph showing a correlation between the pulse width of the scattered light signals and the maximum value of the electric resistance signals in accordance with the present invention.

FIG. 2 shows a correlation of the maximum value of the electric resistance signal obtained by the first detector to the scattered light signal generated period of time obtained by the clock for each of the particles which pass through the pore one after another. The analyzer means classifies the particles based on the correlation. The correlation here actually means a scattergram.

The analyzer means is preferably formed of a microcomputer including CPU, ROM and RAM.

Further the particle analyzer of the present invention may include a comparison unit for comparing the scattered light signal obtained by the second detector means with a first reference value as well as a second reference value larger than the first reference value; a second clock for clocking a first period of time during which the scattered light signal is larger than the first reference value and a second period of time during which the scattered light signal is larger than the second reference value; and a second analyzer for classifying the particle based on a correlation between the first and second periods of time.

Considering a change with time of the scattered light signal obtained by the second detector means, namely a waveform, the waveform of an epithelium cell particle is high from the beginning to the end as shown in FIG. 3(a), that of a mucous string particle is much lower than that of an epithelium cell particle as shown in FIG. 3(b) because the mucous string particle is almost transparent, and that of a cast is high where included matters exist as shown in FIG. 3(c).

When each of the waveforms shown in FIGS. 3(a) to 3(c) is compared with the first reference value, i.e. level I, as well as the second reference value, i.e. level II (level II> level I), the following inequality is obtained on the ratios of the second period of time during which the waveform of the scattered light signal is higher than the level II (a pulse width II) to the first period of time during which the waveform of the scattered light signal is higher than the level 1 (a pulse width I):

the epithelium cell> the cast> the mucous string.

Figure 4:
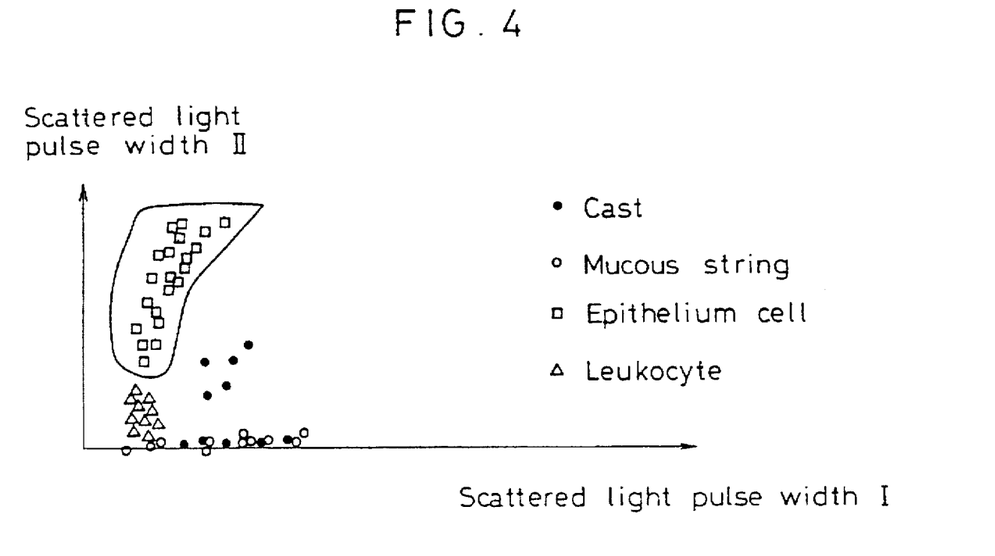
FIG. 4 is a graph showing characteristics of the pulse widths of the scattered light signals in accordance with the present invention.
Figure 5:
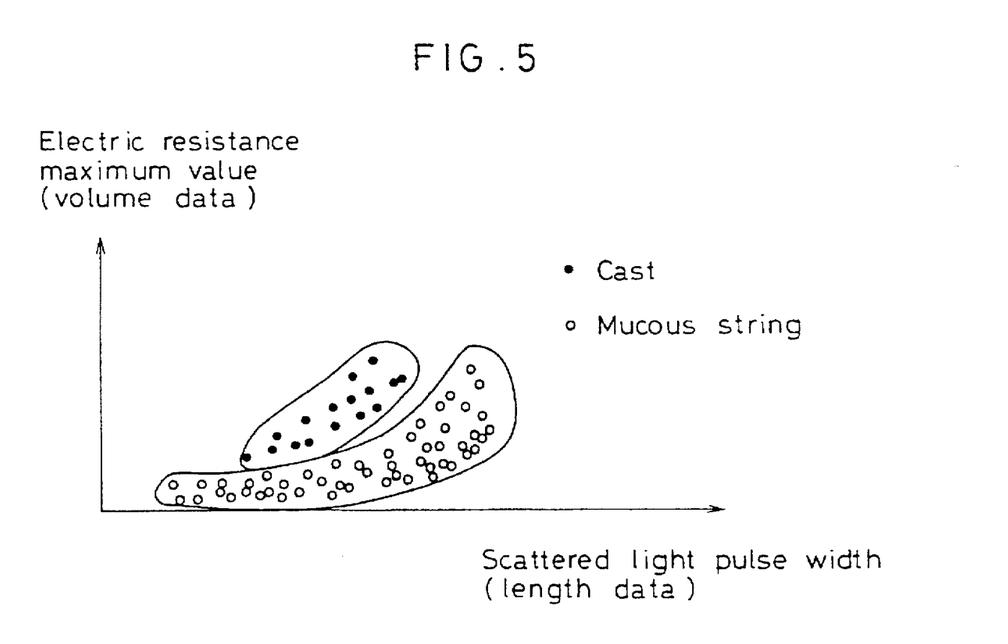
FIG. 5 is a graph showing a correlation between the pulse width of the scattered light signals and the maximum value of the electric resistance signals in accordance with the present invention.

FIG. 4 shows a correlation of the second period of time during which the waveform of the scattered light signal is higher than the level II (the pulse width II) to the first period of time during which the waveform of the scattered light signal is higher than the level I (the pulse width I) of each of the particles which pass through the pore one after another. The correlation enables the second analyzer to easily discriminate the epithelium cells. Therefore, the first analyzer means has only to discriminate the casts and the mucous strings based on the data as shown in FIG. 5 which is obtained by removing the epithelium cells from FIG. 2. The correlation here actually means a scattergram.

Thus, the second analyzer means realizes more precise classification of particles in cooperation with the first analyzer.

A comparator can be used for the comparison unit, a counter (a timer) for the clock, and the second analyzer means can be formed of a microcomputer like the first analyzer.

Still further the particle analyzer of the present invention may comprise a third detector for detecting fluorescence from the particle receiving the beam of light to generate a fluorescence signal representative of an intensity of the fluorescence; a second comparison unit for comparing the fluorescence signal with a third reference value; third clock for clocking a third period of time during which the fluorescence signal is larger than the third reference value; and a third analyzer for classifying the particle based on a correlation between the clocked third period of time and the scattered light signal generated period.

The third detector means serves to detect the fluorescence from the particle receiving the beam of light. Since the wavelength of fluorescence is longer than that of scattered light and the intensity of fluorescence is faint, the third detector is preferably combined with a photomultiplier tube and a filter which, removing scattered light, allows only fluorescence to pass through.

Figure 6A:
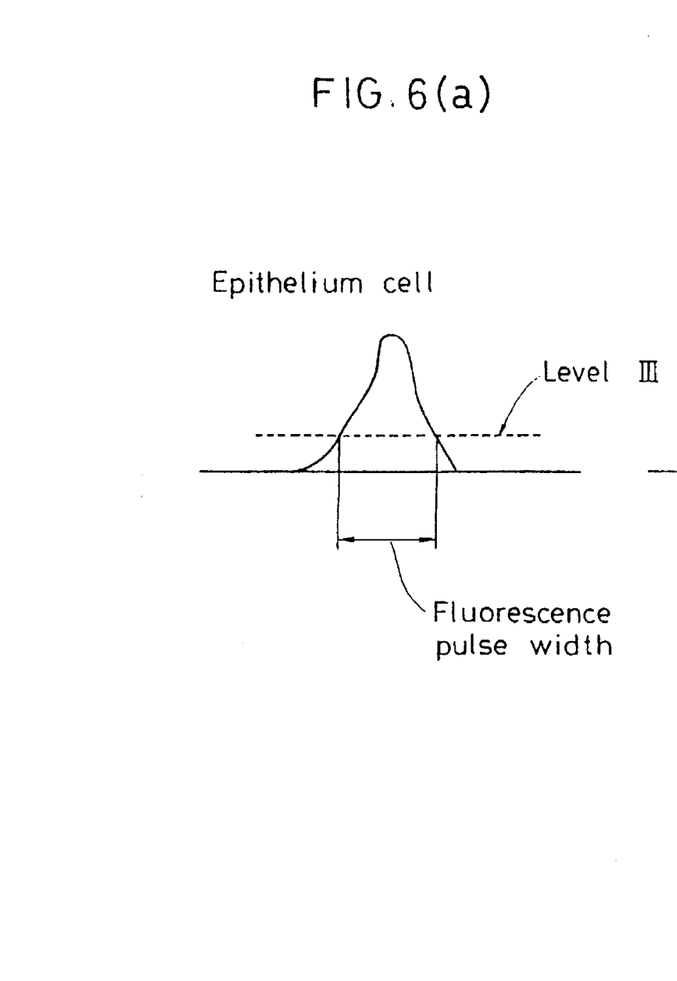
FIGS. 6(a) to 6(c) are views explaining pulse waveforms of the fluorescence signals in accordance with the present invention.
Figures 6B, 6C:
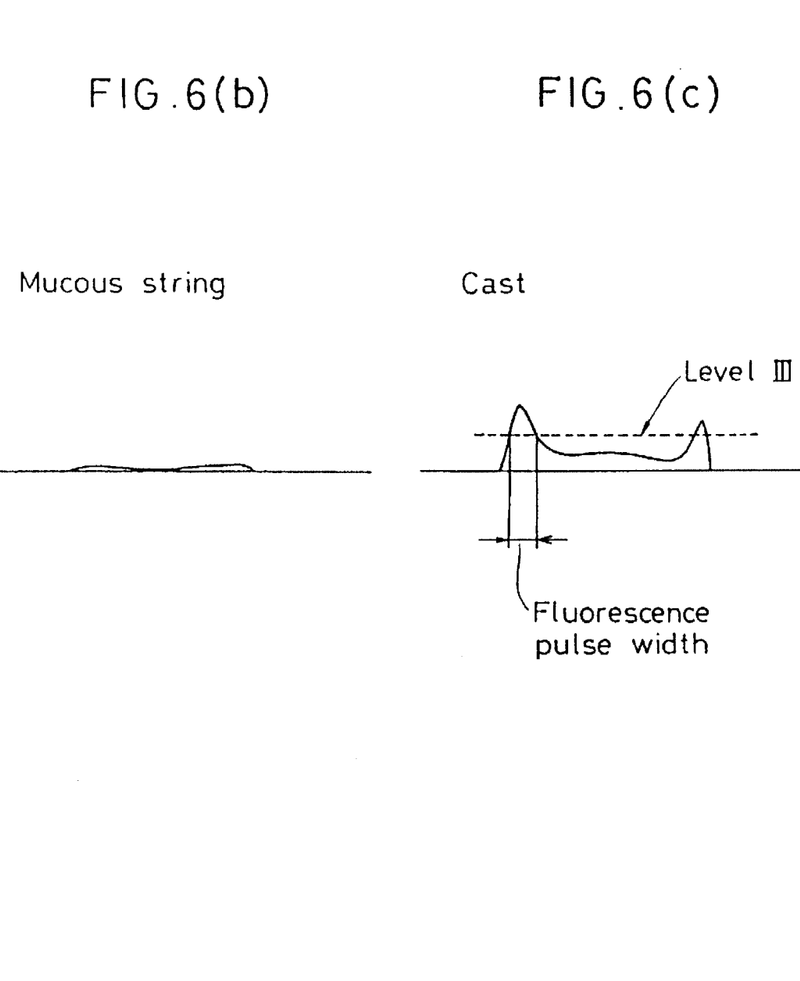

Considering a change with time of the fluorescence signal obtained by the third detector, namely a waveform, the waveform of an epithelium cell particle is high and long as shown in FIG. 6(a) because it is easily dyed with fluorescence dye due to a lot of DNAs contained therein, that of a mucous string particle, as shown in FIG. 6(b), hardly has a wave-shaped form because it does not contain any DNAs, and that of a cast is high as shown in FIG. 6(c) where included matters exist.

When each of the waveforms shown in FIGS. 6(a) to 6(c) is compared with the third reference value (level III), the flowing inequality is obtained on the third period of time during which the waveform of the fluorescence signal is higher than the level III (a fluorescence pulse width):

the epithelium cell> the cast> the mucous string.

Figure 7:
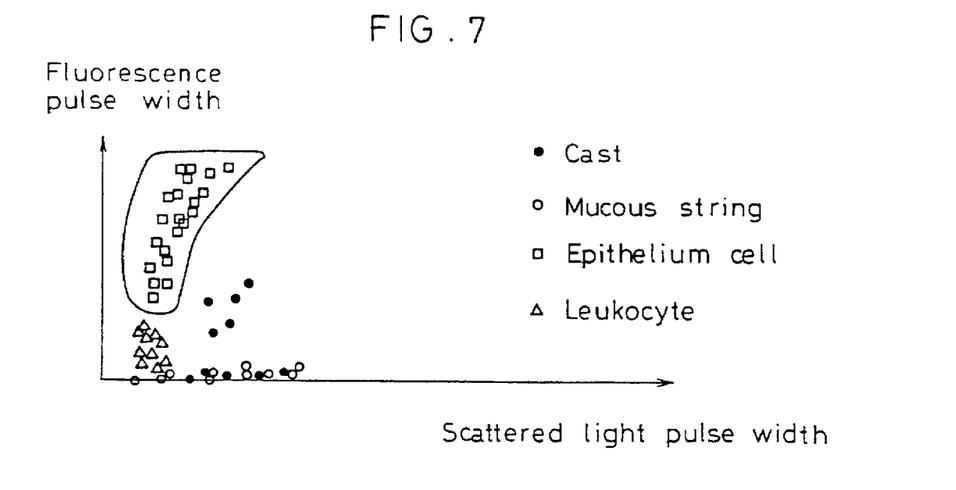
FIG. 7 is a graph showing a correlation between the pulse width of the fluorescence signals and that of the scattered light signals in accordance with the present invention.

FIG. 7 shows a correlation of the period of time during which the waveform of the fluorescence light signal is higher than the level III (the fluorescence pulse width) to the pulse width shown in FIG. 2 of each of the particles which pass through the pore one after another. By firstly discriminating epithelium cells based on the FIG. 7 and then removing the data thereabout from the properties shown in FIG. 2, the casts and the mucous strings are easily discriminated.

A comparator can be used for the second comparison unit, a counter or a timer for the third clock, and the third analyzer means can be formed of a microcomputer including CPU, ROM and RAM.

Yet further the particle analyzer of the present invention may included a peak detector means for detecting a maximum value of the scattered light signal obtained by the second detector; and fourth analyzer means for classifying the particle based on the obtained maximum value.

Considering a waveform of the scattered light of a cast, a cast which contains few included matters is called a glassy cast and nearly transparent, and the peak value of the scattered light thereof is low. On the other hand, a cast containing inclusion bodies which are called granular casts, red cell casts, epithelial casts and the like shows a high peak value.

Figure 8A:
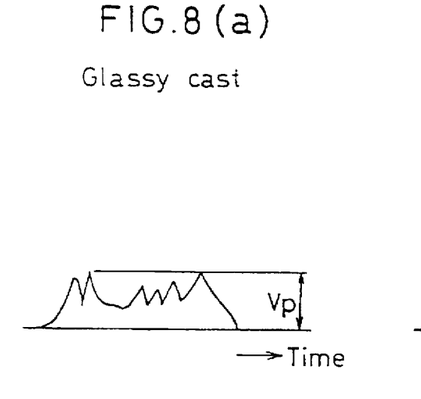
FIGS. 8(a) and 8(b) are views explaining waveforms of the scattered light signals.
Figure 8B:
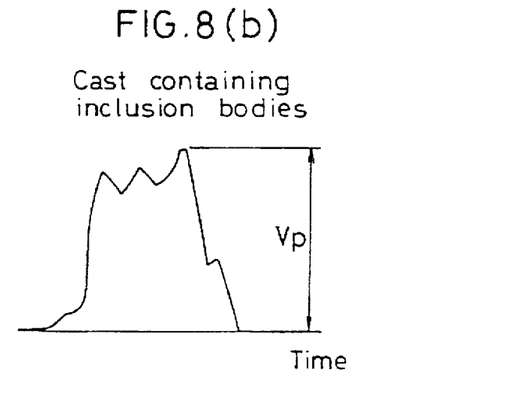

Comparing the maximum value Vp of the scattered light signal of a glassy cast as shown in FIG. 8(a) with the maximum value Vp of the scattered light of a cast containing inclusion bodies as shown in FIG. 8(b), the following result is obtained, which enables the casts to be classified:

the cast with inclusion bodies> the glassy cast

Figure 9:
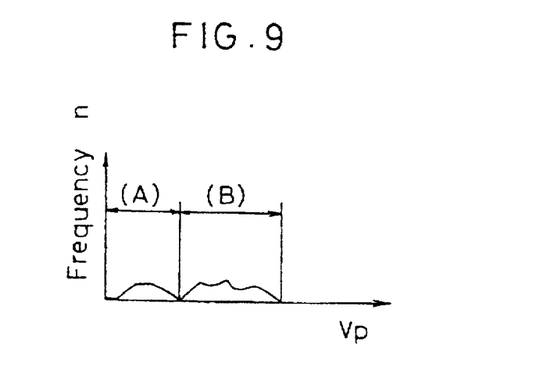
FIG. 9 explains a frequency distribution of the maximum value of the scattered light signals.

FIG. 9 explains an obtained frequency distribution of the maximum values of the waveforms of the scattered light signals, (A) being the distribution area for the glassy casts and (B) being that for the casts containing inclusion bodies. The glassy casts and the casts with inclusion bodies are easily discriminated.

Thus, the fourth analyzer classifies the particles still more precisely in cooperation with the second analyzer.

A peak hold circuit and an A/D converting circuit can be used for the peak detector means and a microcomputer for the fourth analyzer means.

Yet further, the particle analyzer of the present invention may includes a peak detector for detecting a maximum value of the fluorescence signal obtained by the third detector; and a fifth analyzer for classifying the particle based on the obtained maximum value.

Considering a fluorescence waveform of a cast, the glassy cast which contains few included matters is hard to dye and the maximum peak value thereof is low. On the other hand, the cast containing inclusion bodies which are called granular casts, epithelial casts, leukocyte casts and the like has a high peak value because the inclusion bodies are easily dyed with fluorescence dye.

Figure 10A:
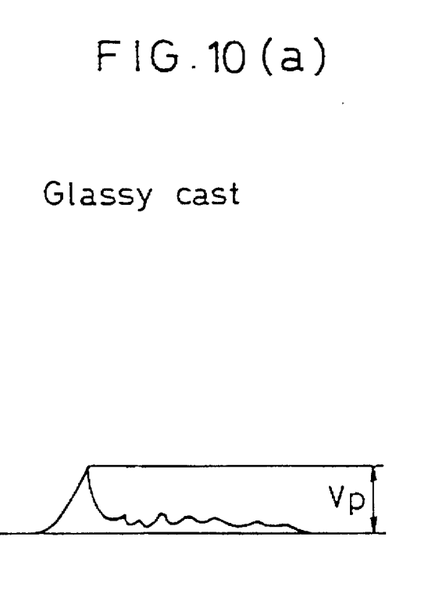
FIGS. 10(a) and 10(b) are views explaining the waveforms of the fluorescence signals.
Figure 10B:
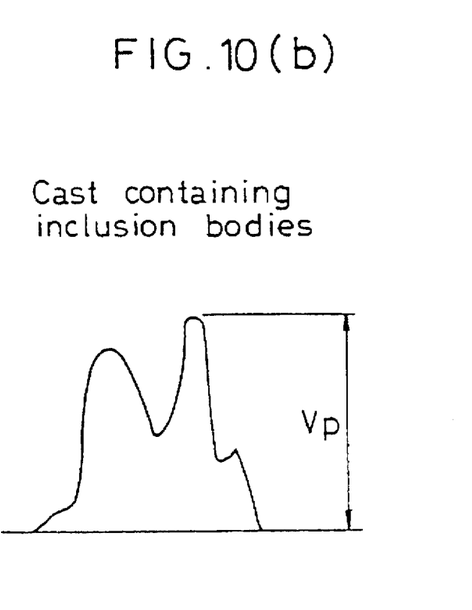

Comparing the maximum value Vp of the fluorescence signal of a glassy cast as shown in FIG. 10(a) with the maximum value Vp of the fluorescence of a cast containing inclusion bodies as shown in FIG. 10(b), the following result is obtained, which enables the casts to be classified:

the cast with inclusion bodies> the glassy cast

Figure 11:
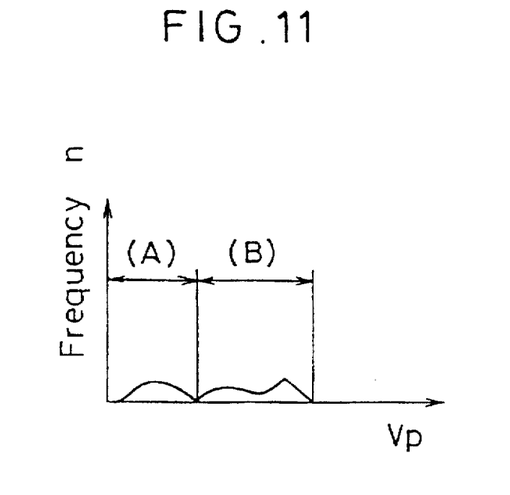
FIG. 11 explains a frequency distribution of the maximum value of the fluorescence signals.

FIG. 11 explains an obtained frequency distribution of the maximum values of the waveforms of the fluorescence signals, (A) being the distribution area for the glassy casts and (B) being that for the casts containing inclusion bodies. The glassy casts and the casts with inclusion bodies are easily discriminated.

Thus, the fifth analyzer means classifies the particles still more precisely in cooperation with the third analyzer.

A peak hold circuit and an A/D converting circuit can be used for the peak detector and a microcomputer for the fifth analyzer.

These and other objects of the present application will become more readily apparent from the detailed description given hereinafter. However, it should be understood that the detailed description and specific examples, while indicating a preferred embodiment of the invention, are given by way of illustration only, since various changes and modifications within the spirit and scope of the invention will become apparent to those skilled in the art from this detailed description.

Figure 12:
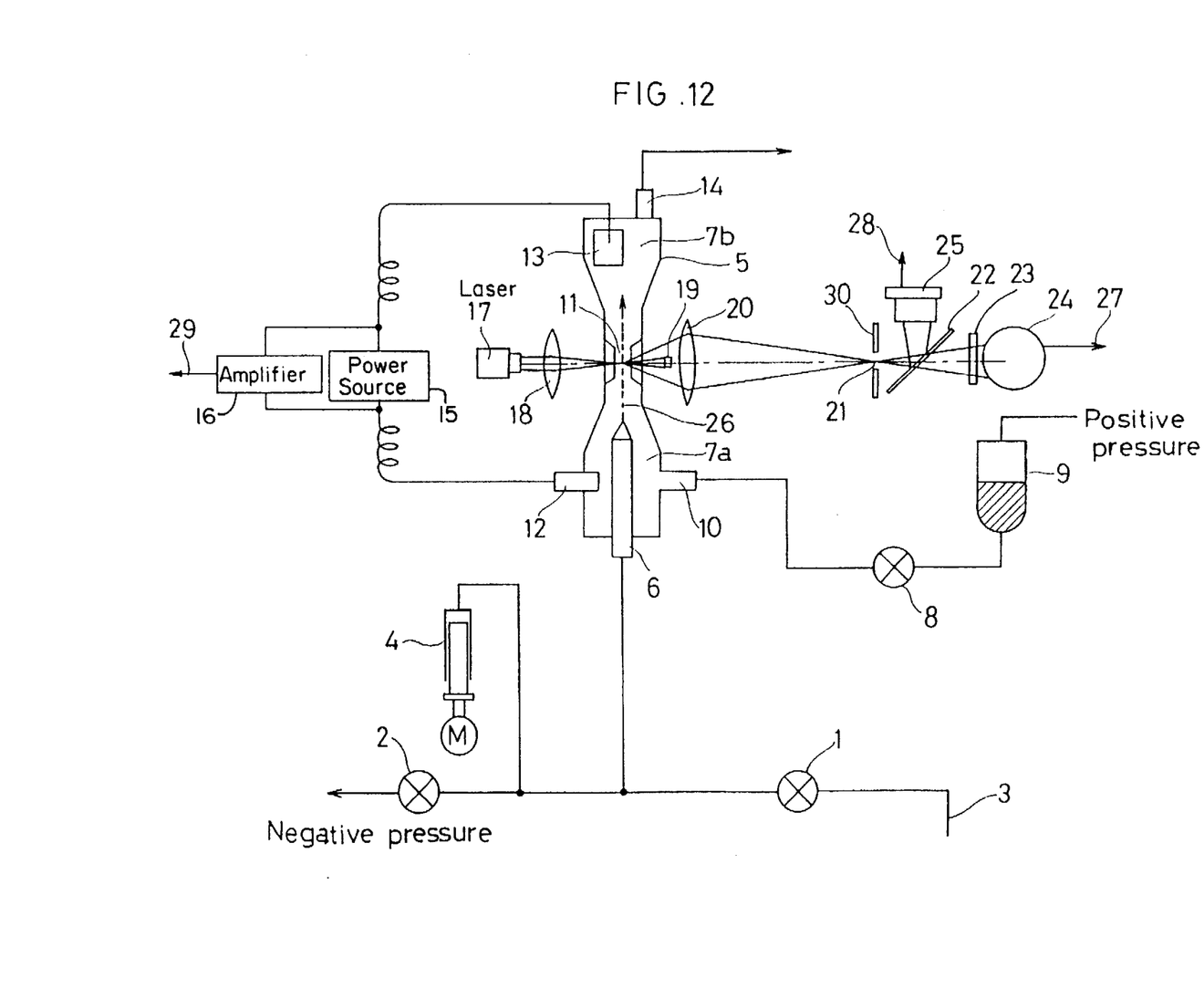
FIG. 12 is a constitutional view of an embodiment in accordance with the present invention.
Figure 13:
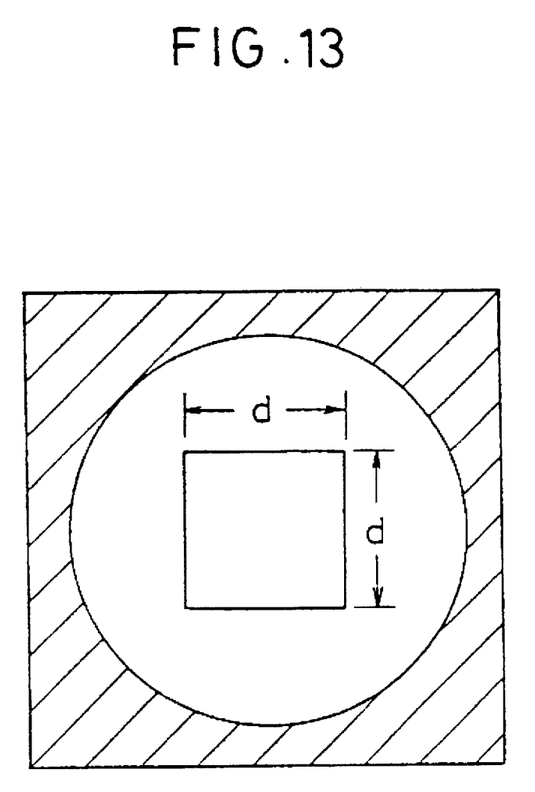
FIG. 13 is a partially sectional view of FIG. 12.

FIG. 12 is a view explaining the constitution of one embodiment according to the present invention the particle analyzer includes valves 1, 2 a suction nozzle 3 for sucking sample liquid processed with pretreatment such as dilution and fluorescence dying from a sample liquid container (not shown in the figure), a syringe, 4 a flow cell, 5 a sample nozzle, 6 a first cell, 7a a second cell, 7b a valve, 8 a sheath liquid container, 9. A feed opening 10 feed the sheath liquid into the first cell 7a, A pore 11 connects the first cell 7a with the second cell 7b which includes an orifice-like part (referred to just as an orifice hereafter), of which the sectional view is shown in FIG. 13. An electrode 12 made of stainless steel is provided in the first cell 7a, and an electrode 13 made of platinum which is provided in the second cell 7b, A discharge opening 141D provided for the second cell 7b, A direct constant current power source 151D connected between the electrodes 12 and 13, the electrode 12 being negative and the electrode 13 being positive. An amplifier 16 amplifies voltage output from the power source 15 and outputs it as a signal 29.

Also included is a laser light source, 17 a condenser lens, 18 a beam stopper, 19 a collector lens, 20 a pinhole, 21 a dichroic mirror, 22 a filter, 23 a photomultiplier tube 24, a photodiode, 25 a flow of sample liquid 26 from the sample nozzle 6 and a shield 30 with the pinhole 21.

In a device having the above described constitution, when the valves 1 and 2 are opened for a predetermined time, the sample liquid flows from the suction nozzle and fills between the valves 1 and 2 by negative pressure.

Then, the syringe 4 pushes the sample liquid between the valves 1 and 2 at a fixed flow rate toward the sample nozzle 6, from which the sample liquid is extruded to the first cell 7a.

At the same time, by opening the valve 8, sheath liquid is fed into the first cell 7a. Thus the sample liquid is enveloped by the sheath liquid, then forming a fine sheath flow by the orifice 11. The sectional view of the orifice 11, as shown in FIG. 13, has a square hole of which a side d is from 100 to 300 μm and is made of optical glass including quartz glass.

The length of the hole is practically preferred to be from 200 to 1,000 μm, which is longer than a particle to be determined and allows an optical axis adjustment.

The sheath flow thus formed enables the particles contained in the sample liquid to flow through the orifice 11 one after another in a row. The sample and the sheath liquid which have passed through the orifice 11 are discharged by the discharge opening 14 provided for the second cell 7b.

The electric resistance between the electrodes 12 and 13 is determined by the electric conductivity of the sheath liquid, the area of the sectional square of the hole of the orifice 11, the electric conductivity of the sample liquid and the diameter of the flow of the sample liquid.

By sending an electric current between the electrodes 12 and 13 from the direct constant power source 15, a d.c. voltage is generated which is determined by the electric resistance and the current strength between the electrodes 12 and 13. Since the electric resistance between both the ends of the orifice 11 changes when a particle passes through the orifice 11, the voltage generated between the electrodes 12 and 13 changes in a pulse during the passage of the particle, and the maximum value of the change or the peak value of the pulse is in proportion to the size of the particle which passes though the orifice 11. The amplifier 16 amplifies the change and outputs it as an electric resistance signal 29 which is an analog pulse signal.

In the meantime, the flow of the sample liquid 26 passing through the orifice 11 receives a laser beam which is generated by the laser light source 17 and then condensed into an oval by the condenser lens 18. The size of the oval is, in the direction of the flow of the sample liquid, almost the same as the diameter of a particle to be determined, e.g. around 10 μm, and, in the right-angled direction to the flow of the sample liquid, sufficiently larger than the diameter of a particle to be determined, e.g. from 100 to 400 μm.

A laser beam which does not hit a particle and gets through the flow cell 5 is stopped by the beam stopper 19. The forward scattered light and the forward fluorescence irradiated by a particle which receives the laser beam are collected by the collector lens 20, then pass through the pinhole 21 of the shield 30 and reach the dichroic mirror 22.

The fluorescence of which the wavelength is longer than the scattered light directly goes through the dichroic mirror 22, and, after residual scattered light is removed by the filter 23, is detected and output as a fluorescence signal 27, which is an analogue pulse signal, by the photomultiplier tube 24. Meanwhile, the scattered light, reflected by the dichroic mirror 22, is received and output as a scattered light signal 28, which is an analog pulse signal, by the photodiode 25.

Figure 14:
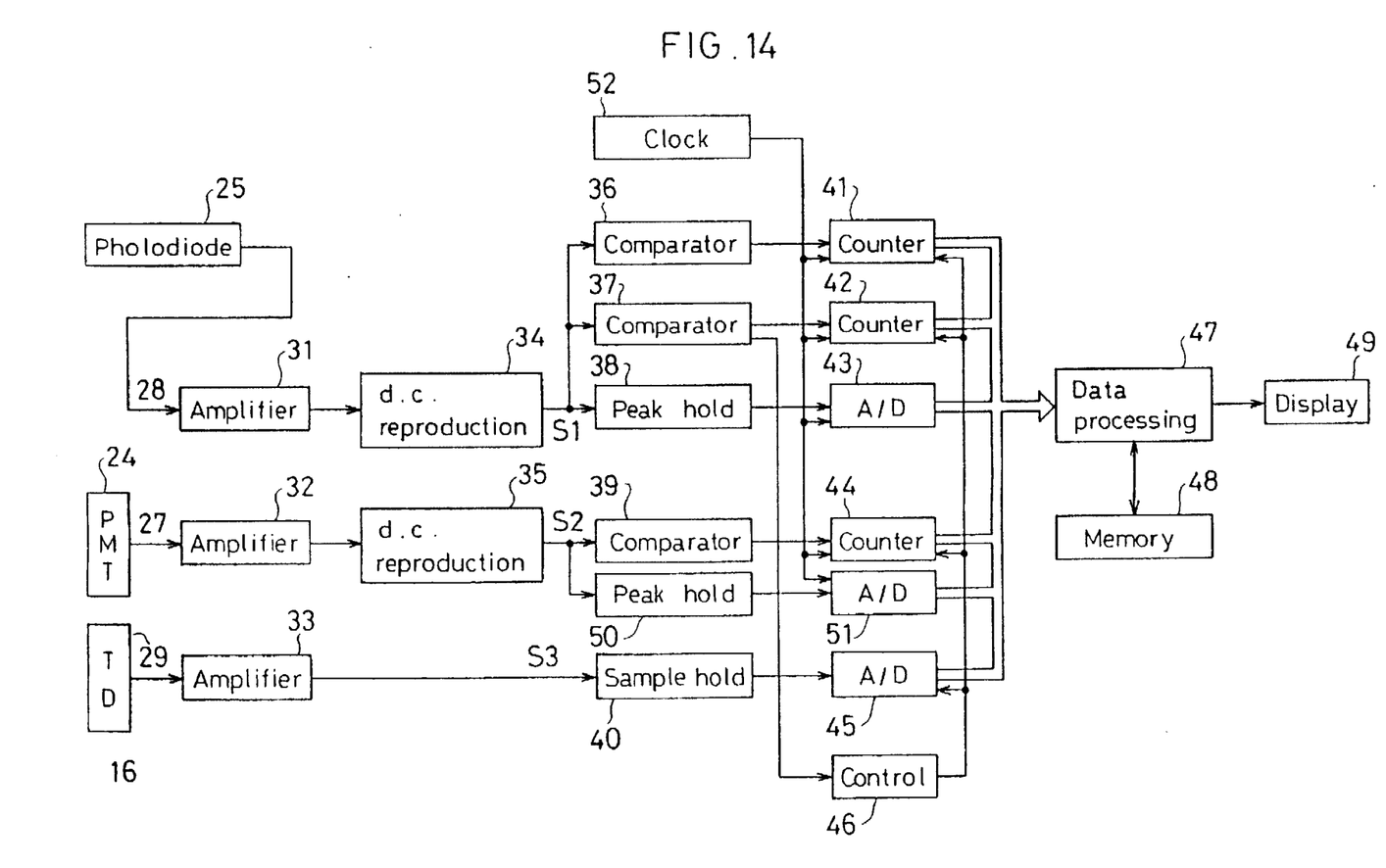
FIG. 14 is a block diagram explaining the signal processing circuit of an embodiment in accordance with the present invention.

FIG. 14 is a block diagram explaining the processing circuit for processing the fluorescence signal 27, the scattered light signal 28 and the electric resistance signal 29 obtained as described above. Reference numerals 31 to 33 denote amplifiers, 34 and 35 d.c. reproduction circuits, 36, 37 and 39 comparators, 38 and 50 peak hold circuits, 52 a clock generator, 41, 42 and 44 counters, 43, 45 and 51 A/D converters, 46 a control circuit, 47 a data processing unit, 48 a memory, 49 a display and 40 a sample hold circuit.

A signal processing operation in such a construction will be hereafter described.

The scattered light pulse signal 28 is amplified by the amplifier 31 and the d.c. level thereof is fixed by the d.c. reproduction circuit 34. A pulse signal S1 output by the d.c. reproduction circuit 34 is compared by the comparators 36 and 37 with the respective threshold levels and the period of times during which the pulse signal S1 is over the threshold levels, i.e. pulse widths, are clocked by the counters 41 and 42. By setting the threshold level of the comparator 36 to such a level as to detect a mucous string, i.e. level 1 in FIG. 3, and that of the comparator 37 to such a level as to detect a cast, i.e. level II in FIG. 3, two kinds of pulse widths, namely the pulse widths I and II in FIG. 3, are obtained. The maximum value of the scattered light is caught by the peak hold circuit 38 and converted from analog to digital by the A/D converter 43.

The fluorescence pulse signal 27 is amplified by the amplifier 32 and the d.c. level thereof is fixed and output as a pulse signal S2 by the d.c. reproduction circuit 35. The pulse signals 2 is compared by the comparator 39 with the threshold level thereof, i.e. level III in FIG. 6, and the period of time during which the pulse signal S2 is over the threshold level is clocked by the counter 44, thus the pulse width, i.e. the fluorescence pulse width in FIG. 6, being obtained. Meanwhile the maximum value of the fluorescence signal 27 is caught by the peak hold circuit 50 and converted to digital by the A/D converter 51.

The electric resistance pulse signal 29 is amplified by the amplifier 33, and the peak value (the maximum peak value) thereof is held by the sample hold circuit 40 and converted to digital by the A/D converter 45.

Digitized output signals from each of the counters 41,42 and 43, and each of the A/D converters 43, 45 and 51 are sent to the data processing unit 47 for particle classification: Based on the scattergrams (the correlations) as shown in FIGS. 2, 4, 5 and 7 and the frequency distributions shown in FIGS. 9 and 11, epithelium cells, casts, mucous strings, glassy casts and casts with inclusion bodies are classified. The classified particles are then counted and changed in terms of the number per microliter of the sample. The result is displayed on the display 49 as well as is stored in the memory 48 together with the scattergrams.

In place of the forward scattered light and forward fluorescence used in the above embodiment, side scattered light and side fluorescence can also be used. The similar result can be obtained when the pulse width of the electric resistance waveform is utilized for obtaining length data of particles.

The present invention has realized an easy classification of particles contained in urine such as casts, mucous strings, epithelium cells and the like by obtaining a correlation between length data and volume data about the particles, and also improved the precision of classification of particles by obtaining a correlation in the scattered light intensity and the fluorescence intensity from the particles.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A particle analyzer comprising:
   a flow cell including first and second cells for containing electrolyte, the first and second cells being connected to each other by a pore to allow particles of various biological types to flow from the first cell to the second cell through the pore;

a first and second electrodes provided in the electrolyte in the first and second cells respectively;

first detecting means for detecting an electric resistance between the first and second electrodes which changes according as the particle passes through the pore to generate an electric resistance signal representative of the electric resistance;

a light source for emitting a beam of light to the flowing particle;

second detecting means for detecting scattered light from the particle receiving the beam of light to generate a scattered light signal representative of an intensity of the scattered light;

clock means for clocking a period of time during which the scattered light signal is generated; and analysis means for classifying the particle as a particular type of the various biological types based on a correlation between the electric resistance signal and the clocked period of time.

2. The particle analyzer according to claim 1, further comprising:

comparison means for comparing the scattered light signal obtained by the second detecting means with a first reference value as well as a second reference value larger than the first reference value;

second clock means for clocking a first period of time during which the scattered light signal is larger than the first reference value and a second period of time during which the scattered light signal is larger than the second reference value; and second analysis means for classifying the particle based on a correlation between the first and second periods of time.

3. The particle analyzer according to claim 2, further comprising means for eliminating particles identified by said second analysis means from consideration by said analysis means.

4. The particle analyzer according to claim 2, further comprising:

peak detecting means for detecting a maximum value of the scattered light signal obtained by the second detecting means; and fourth analysis means for classifying the particle based on the obtained maximum value.

5. The particle analyzer according to claim 1, further comprising:

third detecting means for detecting fluorescence from the particle receiving the beam of light to generate a fluorescence signal representative of an intensity of the fluorescence;

second comparison means for comparing the fluorescence signal means with a third reference value;

third clock means for clocking a third period of time during which the fluorescence signal is larger than the third reference value; and third analysis means for classifying the particle based on a correlation between the clocked third period of time and the scattered light signal generated period of time.

6. The particle analyzer according to claim 5, further comprising;

peak detecting means for detecting a maximum value of the fluorescence signal obtained by the third detecting means; and fifth analysis means for classifying the particle based on the obtained maximum value.

7. The particle analyzer according to claim 5, further comprising means for eliminating particles identified by said third analysis means from consideration by said analysis means.

8. A particle analyzer comprising:

a flow cell including first and second cells for containing electrolyte, the first and second cells being connected to each other by a pore to allow particles of various biological types to flow from the first cell to the second cell through the pore;

a light source for emitting a beam of light to the flowing particle;

a detector for detecting scattered light from the particle receiving the beam of light to generate a scattered light signal representative of an intensity of the scattered light;

comparison means for comparing the scattered light signal obtained by the detector with a first reference value as well as a second reference value larger than the first reference value;

a clock for clocking a first period of time during which the scattered light signal is larger than the first reference value and a second period of time during which the scattered light signal is larger than the second reference value; and analysis means for classifying the particle based on a correlation between the first and second periods of time.

9. The particle analyzer according to claim 8, further comprising:

peak detecting means for detecting a maximum value of the scattered light signal obtained by the second detecting means; and fourth analysis means for classifying the particle based on the obtained maximum value.

10. A particle analyzer comprising:

a flow cell including first and second cells for containing electrolyte, the first and second cells being connected to each other by a pore to allow particles of various biological types to flow from the first cell to the second cell through the pore;

a light source for emitting a beam of light to the flowing particle;

a first detector for detecting scattered light from the particle receiving the beam of light to generate a scattered light signal representative of an intensity of the scattered light;

a clock for clocking a period of time during which the scattered light signal is generated;

a second detector for detecting fluorescence from the particle receiving the beam of light to generate a fluorescence signal representative of an intensity of the fluorescence;

a comparator for comparing the fluorescence signal means with a reference value;

another clock for clocking another period of time during which the fluorescence signal is larger than the reference value; and analysis means for classifying the particle based on a correlation between the another clocked period of time and the scattered light signal generated period of time.

11. The particle analyzer according to claim 10, further comprising:

peak detecting means for detecting a maximum value of the fluorescence signal obtained by the second detector; and second analysis means for classifying the particle based on the obtained maximum value.

12. A method for analyzing particles in an electrolyte comprising the steps of:

connecting first and second cells for containing electrolyte to each other to allow particles of various types to flow from the first cell to the second cell;

providing first and second electrodes in the electrolyte in the first and second cells respectively;

detecting an electric resistance between the first and second electrodes which changes according as the particle passes through the pore to generate an electric resistance signal representative of the electric resistance;

emitting a beam of light to the flowing particle;

sensing scattered light from the particle receiving the beam of light to generate a scattered light signal representative of an intensity of the scattered light;

clocking a period of time during which the scattered light signal is generated; and classifying the particle as a particular type of the various types based on a correlation between the electric resistance signal and the clocked period of time.

13. The method according to claim 12, further comprising:

comparing the scattered light signal obtained during said sensing step with a first reference value as well as a second reference value larger than the first reference value; and clocking a first period of time during which the scattered light signal is larger than the first reference value and a second period of time during which the scattered light signal is larger than the second reference value;

said classifying step further includes classifying the particle based on a correlation between the first and second periods of time.

14. The method according to claim 13, further comprising:

eliminating particles identified by the correlation between the first and second periods of time from consideration by classifying by the correlation between the electric resistance signal and the clocked period of time.

15. The according to claim 13, further comprising peak detecting a maximum value of the scattered light signal obtained by said sensing step, wherein said classifying step further includes classifying the particle based on the obtained maximum value.

16. The method according to claim 12, further comprising:

generating a fluorescence signal representative of an intensity of the fluorescence from the particle receiving the beam of light;

comparing the fluorescence signal means with a reference value; and clocking another period of time during which the fluorescence signal is larger than the reference value;

said classifying step further including classifying the particle based on a correlation between the another clocked period of time and the scattered light signal generated period of time.

17. The method according to claim 16, further comprising:

eliminating particles identified by the correlation between the another clocked period of time and the scattered light signal generated period of time from consideration by classifying by the correlation between the electric resistance signal and the clocked period of time.

18. The method according to claim 16, further comprising peak detecting a maximum value of the fluorescence signal obtained by the generating step, wherein said classifying step includes classifying the particle based on the obtained maximum value.

\* \* \* \* \*